United States Patent
Fujiwara et al.

(10) Patent No.: US 9,823,178 B2
(45) Date of Patent: Nov. 21, 2017

(54) FLOW CYTOMETER, PARTICLE ANALYZER, AND FLOW CYTOMETRIC METHOD

(71) Applicant: Sysmex Corporation, Kobe-shi, Hyogo (JP)

(72) Inventors: Takao Fujiwara, Kobe (JP); Seiichiro Tabata, Kobe (JP); Fumiya Futamatsu, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 0 days.

(21) Appl. No.: 14/805,009

(22) Filed: Jul. 21, 2015

(65) Prior Publication Data

US 2016/0025611 A1 Jan. 28, 2016

(30) Foreign Application Priority Data

Jul. 22, 2014 (JP) .................. 2014-149021

(51) Int. Cl.
| | |
|---|---|
| *G01N 33/48* | (2006.01) |
| *G01N 15/14* | (2006.01) |
| *G01J 1/04* | (2006.01) |
| *G02B 3/04* | (2006.01) |
| *G02B 3/06* | (2006.01) |
| *G02B 27/09* | (2006.01) |
| *G02B 19/00* | (2006.01) |

(52) U.S. Cl.
CPC ........ *G01N 15/1434* (2013.01); *G01J 1/0422* (2013.01); *G01N 15/1459* (2013.01); *G02B 3/04* (2013.01); *G02B 3/06* (2013.01); *G02B 19/0014* (2013.01); *G02B 27/0966* (2013.01)

(58) Field of Classification Search
CPC .......... G01N 15/1434; G01N 15/1404; G01N 15/1459; G01N 15/0205; G01N 2015/1486; G01N 2021/4707
USPC ............................................ 356/335–343, 73
See application file for complete search history.

(56) References Cited

U.S. PATENT DOCUMENTS

| | | | | |
|---|---|---|---|---|
| 4,577,964 | A * | 3/1986 | Hansen, Jr. | ........ G01N 15/0205 356/336 |
| 5,337,082 | A * | 8/1994 | Fredericks | .............. G01S 13/91 342/114 |
| 6,052,236 | A * | 4/2000 | Nakasuji | .................. G02B 3/02 235/462.42 |
| 6,713,019 | B2 * | 3/2004 | Ozasa | ................ G01N 15/1434 356/317 |

(Continued)

FOREIGN PATENT DOCUMENTS

| | | |
|---|---|---|
| CN | 102681171 A | 9/2012 |
| CN | 103 176 226 A | 6/2013 |

(Continued)

*Primary Examiner* — Hoa Pham
(74) *Attorney, Agent, or Firm* — Brinks Gilson & Lione (57) ABSTRACT

A flow cytometer comprises a flow cell configured to induce a flow of a sample containing object particles, a light source, an irradiating optical system configured to irradiate light from the light source on the flow of particles in the flow cell, a detecting part configured to detect light given off from the flow of particles which are irradiated by light. The irradiating optical system comprises a collective lens having an optical axis symmetric aspherical surface on one surface, and a cylindrical surface on the other surface.

20 Claims, 10 Drawing Sheets

(56) References Cited

U.S. PATENT DOCUMENTS

| | | | |
|---|---|---|---|
| 7,468,789 B2* | 12/2008 | Czarnek | G01N 15/1404 356/244 |
| 7,715,006 B2* | 5/2010 | Tabata | G01N 15/1434 356/336 |
| 2004/0246597 A1 | 12/2004 | Ono et al. | |
| 2008/0079929 A1 | 4/2008 | Luo et al. | |
| 2014/0293281 A1* | 10/2014 | Yamamoto | G01N 21/53 356/338 |

FOREIGN PATENT DOCUMENTS

| | | |
|---|---|---|
| EP | 0 886 162 A2 | 12/1998 |
| JP | H11-14922 | 1/1999 |
| JP | 2008-032659 | 2/2008 |

\* cited by examiner

FIG. 5B
Aspheric lens

FIG. 5A
Aspheric lens

FIG. 10A
5th embodiment

FIG. 10B
5th embodiment

FLOW CYTOMETER, PARTICLE ANALYZER, AND FLOW CYTOMETRIC METHOD

CROSS REFERENCE TO RELATED APPLICATIONS

This application claims priority from prior Japanese Patent Application No. 2014-149021, filed on Jul. 22, 2014, entitled "FLOW CYTOMETER, PARTICLE ANALYZER, AND FLOW CYTOMETRIC METHOD".

FIELD OF THE INVENTION

The present invention relates to a flow cytometer, particle analyzer, and flow cytometric method.

BACKGROUND

Flow cytometers are used to analyze particles contained in a sample. In a flow cytometer, a sample containing particles is caused to flow through a flow cell where the particles in the sample flowing through the flow cell are irradiated by light from a light source.

In Japanese Laid-Open Patent Application No. 2008-32659, a collimator lens is used to convert the light from the light source into parallel light rays, a cylindrical lens is used to condense the light in a direction perpendicular to the flow in the flow cell, and a condenser lens is used to condense the light on the flow cell.

In Japanese Laid-Open Patent Application No. 2008-32659, a spherical lens is used as the condenser lens. However, large amount of distortion occurs when the rays are condensed by a single spherical lens, such that a condenser lens having a plurality of glued spherical lenses is usually used in order to reduce the distortion. A cylindrical lens also is usually arranged with spacing as a condenser lens. The thickness of the condenser lens, and the spacing of the condenser lens and the cylindrical lens are restricted by the compactness of the flow cytometer.

SUMMARY OF THE INVENTION

The scope of the present invention is defined solely by the appended claims, and is not affected to any degree by the statements within this summary.

The flow cytometer of a first aspect of the present invention includes a flow cell configured to induce a flow of a sample containing object particles; a light source; an irradiating optical system configured to irradiate light from the light source on the flow of particles in the flow cell; a detecting part configured to detect light given off from the flow of particles which are irradiated by light. In this case the irradiating optical system includes a collective lens having an optical axis symmetric aspheric surface on one surface, and a cylindrical surface on the other surface.

The particle analyzer of a second aspect of the present invention includes the flow cytometer of the first aspect, and an analyzing part configured to process the output from the detecting part, and analyze the object particles in the sample.

The flow cytometric method of a third aspect of the present invention includes flowing a sample containing an object particles through a flow cell, irradiating a flow of particles in the flow cell by condensing the light from a light source through a lens having an optical axis symmetric aspheric surface on one surface and a cylindrical surface on the other surface, and detecting the light given off from the flow in the flow cell.

DETAILED DESCRIPTION OF THE PREFERRED EMBODIMENTS

The preferred embodiments of the present invention will be described hereinafter with reference to the drawings.

The first through fifth embodiments described below use the present invention in an apparatus which performs examination and analysis of blood by detecting the white blood cells, red blood cells, platelets and the like contained in a blood sample, and counting each blood cell.

First Embodiment

Figure 1:
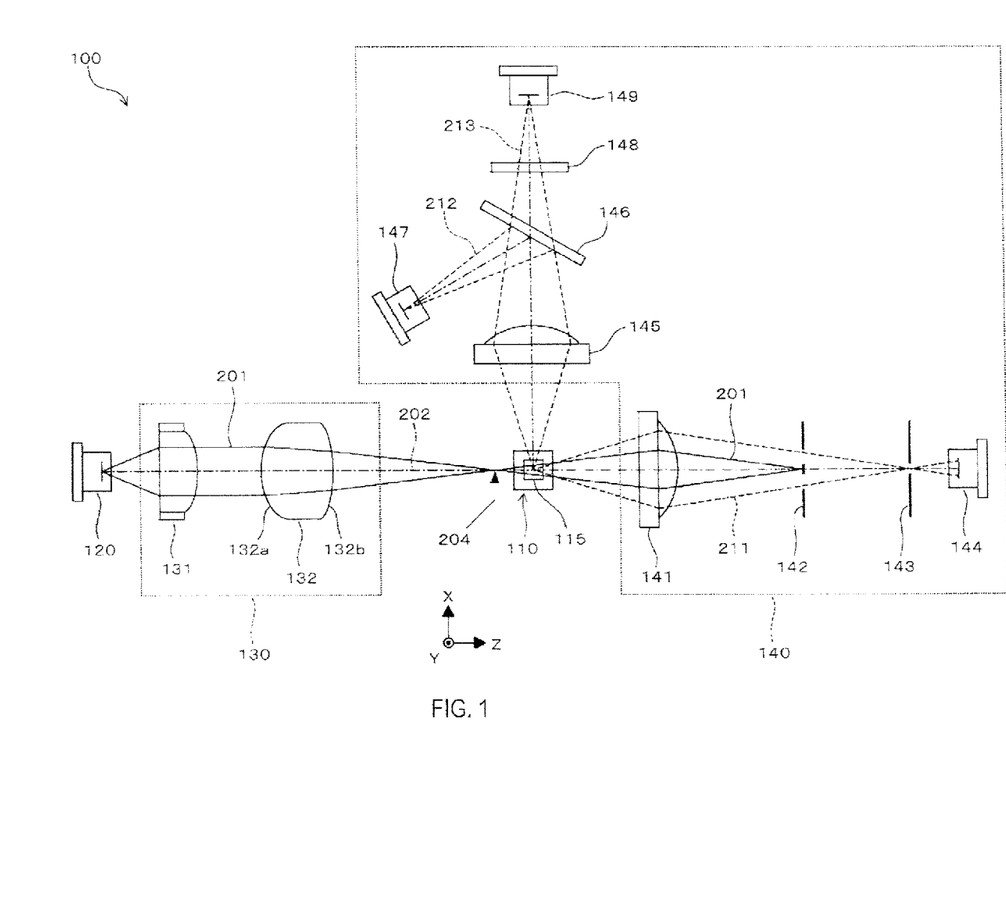
FIG. 1 is a schematic view of the structure of the flow cytometer of a first embodiment viewed in the Y axis negative direction.

As shown in FIG. 1, a flow cytometer 100 is provided with a flow cell 110, a light source 120, an irradiating optical system 130, and a detecting part 140. For the sake of convenience, the mutual intersection of the XYZ axes is shown in FIG. 1.

Figure 2A:
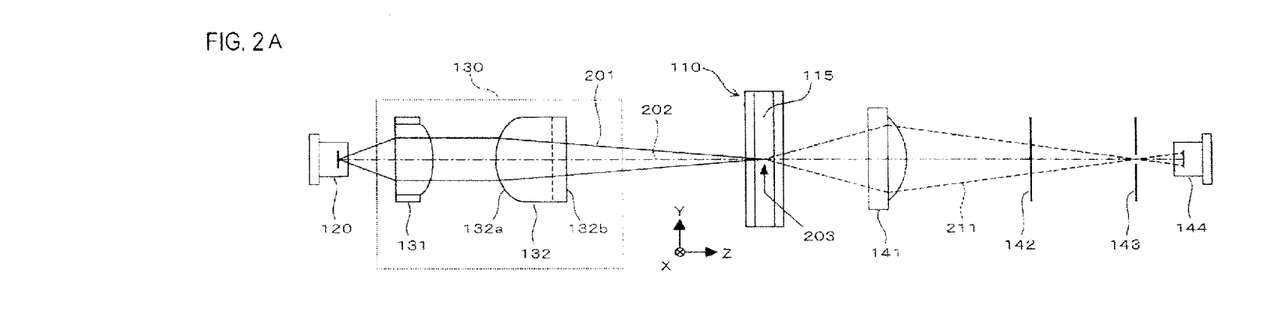
FIG. 2A is a schematic view of the structure of the flow cytometer of a first embodiment viewed in the X axis positive direction.
Figure 2B:
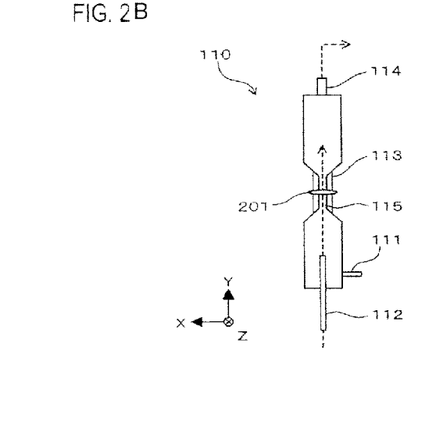
FIG. 2B is a schematic view of the structure of the flow cytometer of the first embodiment.

As shown in FIG. 2B, the flow cell 110 has a sheath fluid supply port 111, a sample nozzle 112, a pore part 113, and a disposal port 114. The sheath fluid supply port 111 supplies sheath fluid into the flow cell 110. The sample nozzle 112 injects a measurement sample upward within the flow cell 110. The measurement sample progresses through a flow path 115 formed in the pore part 113 while encapsulated in the sheath fluid, and toward the disposal port 114. The flow path 115 extends in the Y axis direction. The measurement sample contains particles such as blood cells, and each particle passes through the flow path 115 while aligned in a row.

Returning to FIG. 1, the light source 120 emits laser light 201 in the Z axis positive direction. The laser light 201 has a wavelength of approximately 642 nm. The emission optical axis of the light source 120 matches the optical axis 202 of the irradiating optical system 130.

Figure 2C:
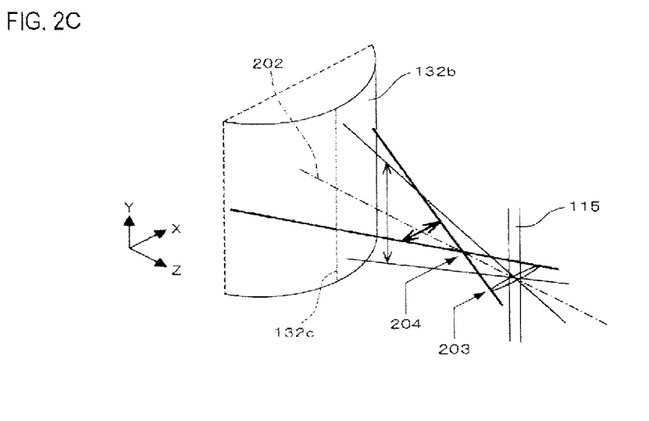
FIG. 2C is a schematic view of the collective lens exit surface and laser light convergence state in the first embodiment.

The irradiating optical system 130 has a collimator lens 131 and a collective lens 132. The collimator lens 131 converts the laser light emitted from the light source 120 to parallel rays. The collective lens 132 is made of glass and has an entrance surface 132a and an exit surface 132b. The entrance surface 132a is an optical axis symmetric aspherical surface, and the exit surface 132b is a convex shape, that is, a cylindrical surface of fixed curvature. The generating line 132c of the cylindrical surface is parallel to the flow path 115, as shown in FIG. 2C. For the sake of convenience, the illustration of the entrance surface 132a of the collective lens 132 is omitted in FIG. 2C. Although the shape of the collective lens 132 is illustrated as rectangular in the XY plane for convenience in FIG. 2C in order to schematically show the effect of the cylindrical surface, the actual external shape is circular. The same is true for FIGS. 7A through 7C below.

As shown in FIGS. 2A and 2C, the laser light 201 is converged by the entrance surface 132a in the Y axis direction, and focused at position 203. Position 203 matches the position of the flow path 115 of the flow cell 110. However, the laser light 201 also is converged by the entrance surface 132a and the exit surface 132b in the X axis direction, and focused at position 204, as shown in FIG. 1 and FIG. 2C Position 204 is on the Z axis negative side from the position of the flow path 115 of the flow cell 110.

As shown in FIGS. 2B and 2C, the laser light 201 irradiates the flow path 115 by a shape which has a smaller width in the Y axis direction than the X axis direction, that is, by a shape which has a width in the direction parallel to the flow path 115 that is smaller than the width in a direction traversing the flow path 115. When an optical axis symmetric aspheric surface is used to focus the laser light 201 at position 203, the spherical aberration is effectively suppressed compared to when a spherical surface is used. The suppression of spherical aberration is described below with reference to FIGS. 4A and 4B and FIGS. 5A and 5B.

In this case, in the plane of the intersection of the optical axis 202 and the entrance surface 132a, the distance from the intersection point is designated r, and the distance from the tangent plane to the entrance surface 132a is designated z. The distance z shows the shape of the optical axis symmetric aspheric surface of the entrance surface 132a. The curvature of the entrance surface 132a is designated c, the $i^{th}$-order aspheric coefficient is designated ai, and the conic constant is designated k. The distance z is regulated by the following even order aspheric surface expression at this time.

$$z = \frac{cr^2}{1 + \sqrt{1-(1+k)c^2r^2}} + \sum_{i=1}^{8} \alpha_i r^{2i} \qquad \text{[Expression 1]}$$

For example, the entrance surface 132a can be designed using the r of the fourth order item or the r of the sixth order item. Thus, the entrance surface 132a can be regulated and designed for a desired optical axis symmetric aspheric surface. In the first embodiment, the optical axis symmetric aspheric surface of the entrance surface 132a is regulated using the r to the fourth order item, and the r of the second order coefficient and the r of the sixth order and subsequent r are designated 0. Each value in the first embodiment, for example, may be set as shown in Table 1 below.

TABLE 1

Parameters of Collective Lens 132 in the First embodiment

| | |
|---|---|
| 1) Entrance surface 132a radius of curvature | 7.665 mm |
| 2) Entrance surface 132a curvature c | 0.13046 |
| 3) Conic constant k | −0.62809 |
| 4) 4th-order aspheric surface coefficient α4 | 0.00001688 |
| 5) Entrance surface 132a focal length | 15.0 mm |
| 6) Exit surface 132b radius of curvature | −65. mm |
| 7) Collective lens 132 refractive index | 1.5110 |

The focal length of the entrance surface 132a, that is, the focal length of the collective lens 132 in the Y axis direction, is set at 5 mm or greater but not more than 100 mm. The focal length of the entrance surface 132a is preferably 5 mm or greater but not more than 70 mm, and ideally 5 mm or greater but not more than 35 mm.

Returning to FIG. 1, a forward scattered light 211, side scattered light 212, and fluorescent light 213 are produced when the particle in the flow path 115 is irradiated by the laser light 201. The forward scattered light 211 issues mainly from the flow cell 110 in the Z axis positive direction. The side scattered light 212 issues mainly from the flow cell 110 in the X axis positive direction and the X axis negative direction. The fluorescent light 213 issues around the periphery of the flow cell 110.

The detecting part 140 is provided with a collective lens 141, beam stopper 142, pinhole 143, light sensor 144, collective lens 145, dichroic mirror 146, light sensor 147, spectral filter 148, and light sensor 149.

The collective lens 141 converges the forward scattered light at the position of the pinhole 143. The collective lens 141 converges the laser light 201, which has passed through the flow cell 110 without irradiating a particle, at the position of the beam stopper 142. The beam stopper 142 transmits the majority of the forward scattered light 211 and blocks the laser light 201 that has passed through the flow cell 110. The light sensor 144 is a photodiode. The light sensor 144 receives the forward scattered light 211 transmitted through the pinhole 143, and outputs signals based on the forward scattered light 211.

The collective lens 145 converges the side scattered light 212 and the fluorescent light 213. The dichroic mirror 146 reflects the side scattered light 212 and transmits the fluorescent light 213. The light sensor 147 is a photodiode. The light sensor 147 receives the side scattered light 212 that was reflected by the dichroic mirror 146, and outputs signals based on the side scattered light 212. The spectral filter 148 transmits only the fluorescent light 213. The light sensor 149 is an avalanche photodiode. The light sensor 149 receives the fluorescent light 213, and outputs signals based on the fluorescent light 213.

Figure 3:
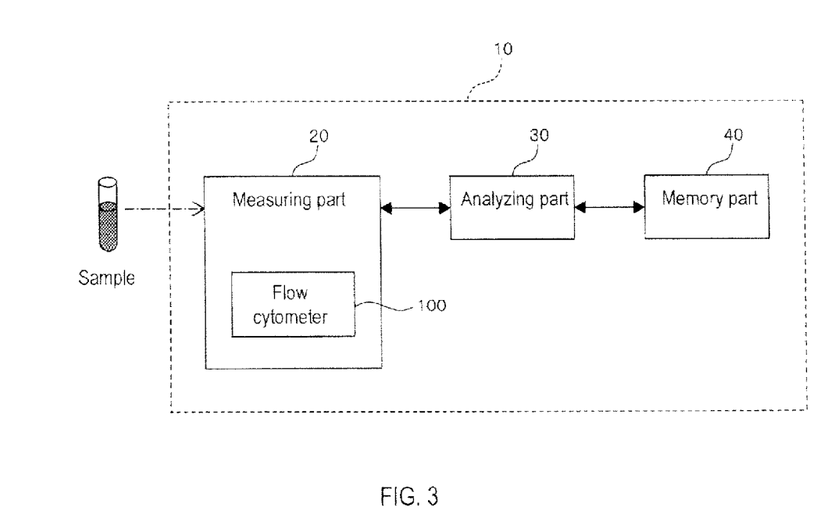
FIG. 3 is a block diagram showing the structure of the particle analyzer of the first embodiment.

As shown in FIG. 3, the particle analyzer 10 is provided with a measuring part 20, analyzing part 30, and memory part 40. The measuring part 20 incorporates a flow cytometer 100.

The measuring part 20 prepares a measurement sample to be used for measurements by mixing reagent and the like with a blood sample of peripheral blood collected from a patient. The measuring part 20 outputs the signals from the light sensors 144, 147, and 149 of the flow cytometer to the analyzing part 30. The analyzing part 30 performs processing to calculate a plurality of characteristics parameters from the waveforms of the received signals. The analyzing part 30 performs analyses based on the calculated characteristics parameters using a computer program stored in the memory part 40, and subsequently stores the analysis results in the memory part 40.

Spherical aberration simulation results are described below referring to FIGS. 4A and 4B, and FIGS. 5A and 5B. The following simulation evaluated the performance of the entrance surface 132a of the collective lens 132. In the simulation, a collective lens 134 configured by an aspheric lens was used instead of the collective lens 132 for purposes of this evaluation. The performance of a collective lens 133 configured by a glued spherical lens also was evaluated as a conventional example for comparison. In the simulation, the sizes of the spot diagrams were obtained and the magnitudes of the spherical aberrations were evaluated when using the collective lens 133 of the conventional example, and when using the collective lens 134.

Figure 4A:
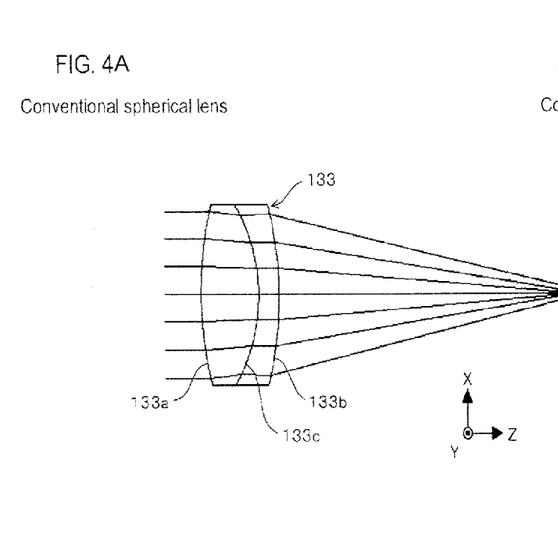
FIG. 4A is a schematic view of a conventional collective lens configured by a spherical lens, and the laser light convergence state.

As shown in FIG. 4A, the collective lens 133 of the conventional example is configured by two glued glass spherical lenses. The entrance surface 133a and the exit surface 133b are both optical axis symmetric spherical surfaces, and the surface 133c formed by gluing the two lenses also is an optical axis symmetric spherical surface. In the simulation, parallel rays impinged the entrance surface 133a, and a spot diagram was obtained at the position of most convergence by the collective lens 133 of the conventional example. The conditions of the simulation are described in Table 2 below.

TABLE 2

Simulation conditions of collective lens 133 (conventional example)

| | |
|---|---|
| 1) Entrance surface 133a radius of curvature | 11.8 mm |
| 2) Entrance surface 133c curvature | −5.9 mm |
| 3) Exit surface 133b radius of curvature | −11.7 mm |
| 4) Collective lens 133 focal length | 15.7 mm |
| 5) Collective lens 133 refractive index | 1.5110 |
| 6) Parallel light wavelength | 642 nm |
| 7) Parallel light radius | 3.24 mm |

Figure 4B:
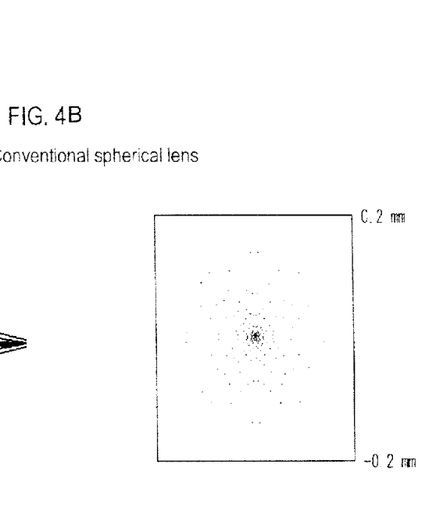
FIG. 4B shows the a spot diagram when a conventional collective lens is configured by a spherical lens.

As shown in FIG. 4B, the spot diagram radius was 0.001161 mm when parallel rays were converged by the collective lens 133 of the conventional example.

Figure 5A:
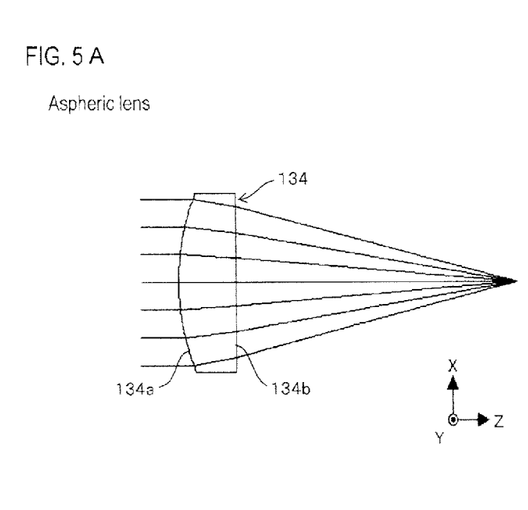
FIG. 5A is a schematic view of a collective lens configured by an aspheric lens, and the laser light convergence state.

As shown in FIG. 5A, the collective lens 134 was configured by a single glass aspheric lens. The entrance surface 134a is an optical axis symmetric aspheric surface identical to the entrance surface 132a of the first embodiment, and was configured as shown in Table 1 (1) through (5) and (7). The exit surface 134b is parallel to the X-Y plane. In the simulation, parallel rays impinged the entrance surface 134a, and a spot diagram was obtained at the position of most convergence by the collective lens 134. The simulation conditions in this case were identical to Table 2 (6) and (7).

Figure 5B:
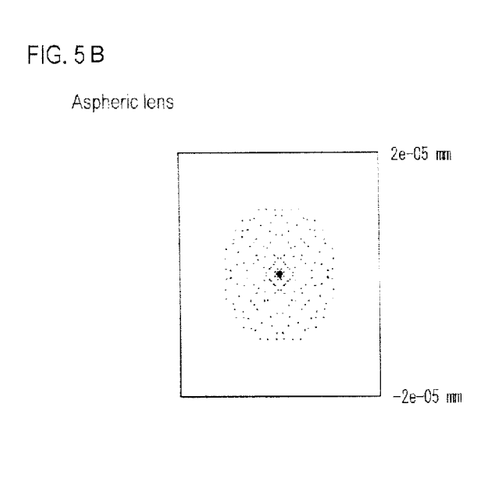
FIG. 5B shows the a spot diagram in the case of a collective lens configured by an aspheric lens.

As shown in FIG. 5B, the spot diagram radius was $4.561 \times 10^{-7}$ mm when parallel rays were converged by the collective lens 134.

According to the results of the simulation, it can be understood that the spherical aberration can be suppressed and laser light converged with a smaller spot diagram in the case of the collective lens 134 configured by an aspheric lens compared to the case of the aspheric lens 133 configured by the spherical lens of the conventional example. In the flow cytometer 100 shown in FIG. 1, the use of the entrance surface 132a which has an optical axis symmetric aspheric surface can be said to more effectively suppress spherical aberration of the laser light 201 because laser light 201 is converged on the flow path 115 of the flow cell 110, compared to the use of the conventional collective lens configured by a spherical surface.

The simulation results of beam intensity at the position of the flow path 115 of the flow cell 110 using the collective lens 132 is described below.

In the simulation, parallel light rays impinged the entrance surface 132a, and beam intensities in the Y axis direction and X axis direction were obtained at the position of the flow path 115 of the flow cell 110. The conditions of this simulation were identical to Table 1 (1) through (7) and Table 2 (6) and (7). The diameter of the flow path 115 was 25 μm.

Figure 6A:
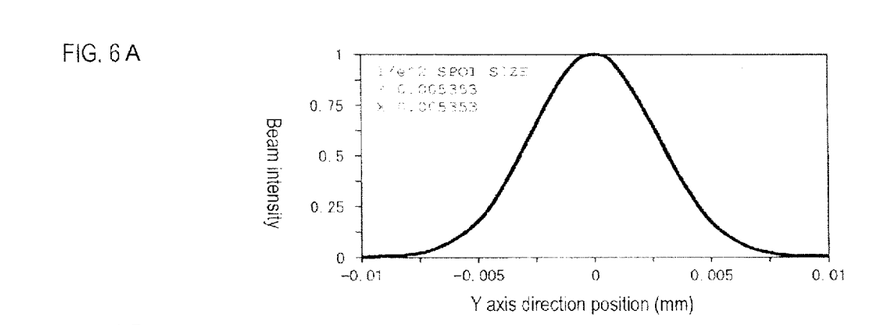
FIG. 6A illustrates the beam strength in the Y axis direction and X axis direction in the first embodiment.
Figure 6B:
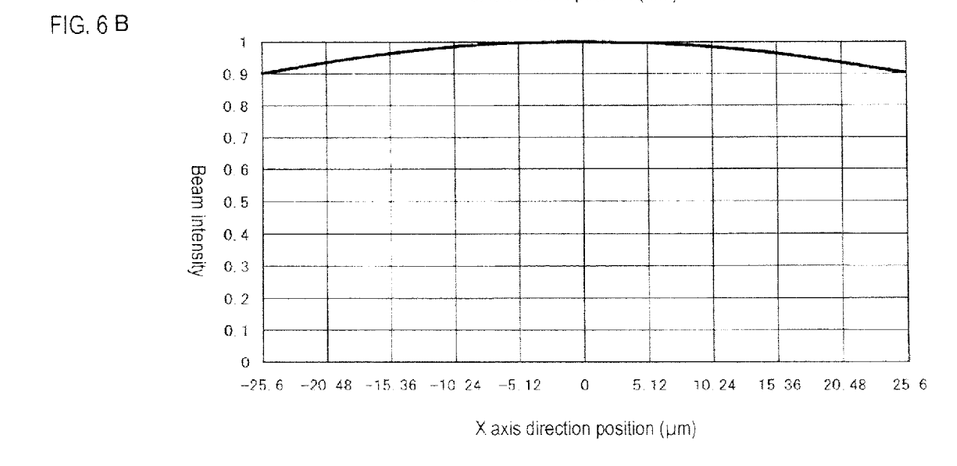
FIG. 6B illustrates the beam strength in the Y axis direction and X axis direction in the first embodiment.

In FIGS. 6A and 6B, the horizontal axis represents the distance from the intersection of the optical axis 202 and the flow path 115, and the vertical axis represents the beam intensity normalized by the maximum value. The shape of the beam intensity in the X axis direction shown in FIG. 6B has a moderate slope in a direction separated from the optical axis compared to the shape of the beam intensity in the Y axis direction shown in FIG. 6A. The beam intensity had a maximum value of 97.4% at the position on the X axis direction 12.5 μm and −12.5 μm, as shown in FIG. 6B. Accordingly, a substantially uniform light irradiated the flow path 115. In this way the shape of the beam intensity in the Y axis direction and the X axis direction in the flow path 115 can be appropriately set for the collective lens 132 so as to detect particles in the measurement sample flowing through the flow path 115.

According to the first embodiment, light from the light source irradiates the flow cell 110 with low aberration and scant distortion without using a plurality of spherical lenses. This permits a reduction in the thickness of the lens for converging the laser light 201. The surface on the opposite side from the cylindrical surface, that is, the entrance surface 132a, can be an optical axis symmetric aspheric surface since a plurality of spherical lenses become unnecessary by using the optical axis symmetric aspheric lens. Since both the shaping and focusing of laser light 201 can be realized by a single collective lens 132, the number of lenses in the irradiation optical system 130 can be reduced and the irradiation optical system 130 can be made more compact. The members and structures for installing and holding lenses, such as holders and the like, can be similarly reduced by the reduction of the number of lenses in the irradiating optical system 130. Therefore, the space for arranging the irradiating optical system 130 can be greatly reduced, and as a result the flow cytometer 100 can be made effectively more compact.

According to the first embodiment, the entrance surface 132a and the exit surface 132b of the collective lens 132 are configured by an optical axis symmetric aspheric surface and a cylindrical surface, respectively. Therefore, the lens surfaces of the collective lens 132 can be designed so that the laser light 201 emitted by the light source 120 irradiates the flow path 115 of the flow cell 110 in a low aberration state with scant distortion.

According to the first embodiment, the optical axis symmetric aspheric surface of the entrance surface 132a has a shape configured to converge the entering laser light 201 at the position 203. The cylindrical surface of the exit surface 132b has a shape configured to shape the laser light 201 irradiating the flow path 115 of the flow cell 110 so that the width in a direction parallel to the flow path 115 is less than the width on a direction intersecting the flow path 115. Therefore, when the functions are divided for each surface of the collective lens 132, the design and fabrication of each surface of the collective lens 132 is facilitated.

According to the first embodiment, the cylindrical surface of the exit surface 132b has a convex shape. Therefore, the focus position of the laser light 201 in the direction intersecting the flow path 115 becomes the position 203 on the light source 120 side of the flow path 115. Hence, the irradiating optical system 130 can be made more compact.

According to the first embodiment, there is no position shift around the optical axis between the entrance surface 132a and the exit surface 132b due to the optical axis symmetric shape of the entrance surface 132a. The expected performance is secured in the collective lens 132 without fabricating the collective lens 132 by strictly managing the rotational positions of the entrance surface and the exit surface.

Second Embodiment

Figure 7A:
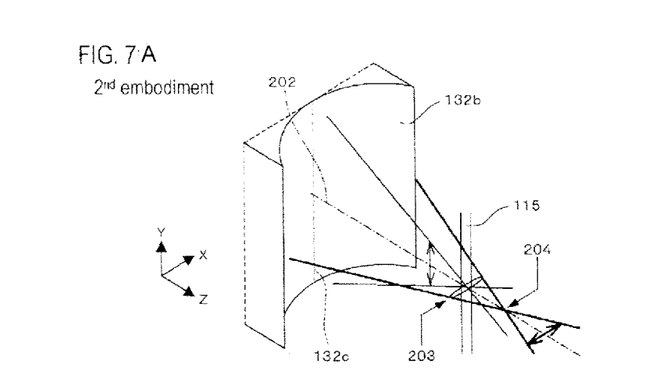
FIG. 7A is a schematic view of the collective lens exit surface and laser light convergence state in a second embodiment.

The flow cytometer of the second embodiment has a structure identical to the flow cytometer of the first embodiment with the exception that the shape of the exit surface of the collective lens 132 is different. As shown in FIG. 7A, in the second embodiment the exit surface 132b of the collective lens 132 is a cylindrical surface of which has a concave shape and constant curvature compared to the first embodiment.

The laser light 201 in this case is converged by the entrance surface 132a in the Y axis direction, and focused at the position 203. Position 203 matches the position of the flow path 115 of the flow cell 110. On the other hand, the laser light 201 is converged by the entrance surface 132a in the X axis direction, diffused by the exit surface 132b, and focused at position 204. Position 204 is on the Z axis positive side from the position of the flow path 115 of the flow cell 110. In the second embodiment, therefore, the laser light 201 irradiates the flow path 115 so that the width of the laser light 201 in a direction parallel to the flow path 115 is less than the width in a direction intersecting the flow path 115 similar to the first embodiment.

In the second embodiment, the entrance surface 132a is designed to converge the light on the flow path 115 similar to the first embodiment. Accordingly, the entrance surface 132a markedly suppresses spherical aberration identically to FIGS. 5A and 5B. In the second embodiment, the lens surfaces of the collective lens 132 can be designed so that the laser light 201 irradiates the flow path 115 of the flow cell 110 in a low aberration state with scant distortion.

The simulation results of beam intensity at the position of the flow path 115 of the flow cell 110 using the collective lens 132 of the second embodiment is described below.

In the simulation, parallel light rays impinged the entrance surface 132a, and beam intensities in the Y axis direction and X axis direction were obtained at the position of the flow path 115 of the flow cell 110. The conditions of this simulation were identical to Table 1 (1) through (5) and Table 2 (6) and (7), and the radius of curvature of the exit surface 132b was 65 mm. The diameter of the flow path 115 was 25 µm.

Figure 8A:
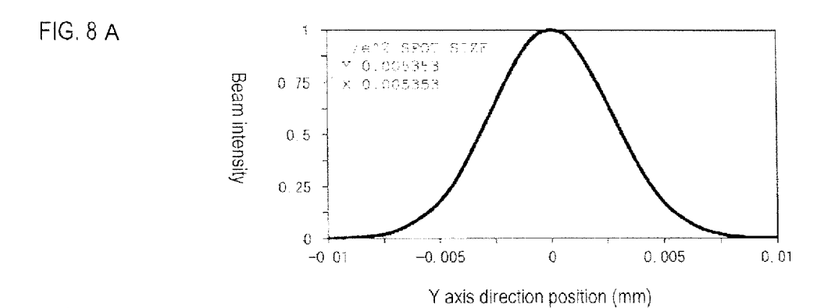
FIG. 8A illustrates the beam strength in the Y axis direction and X axis direction in the second embodiment.
Figure 8B:
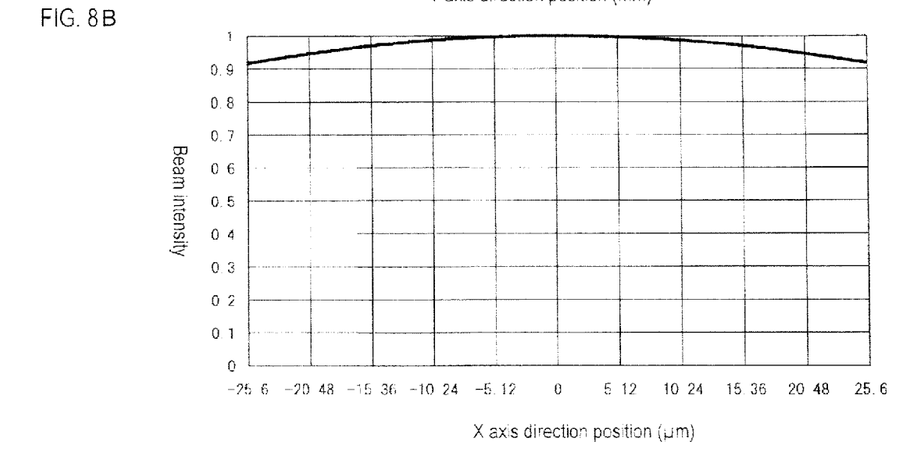
FIG. 8B illustrates the beam strength in the Y axis direction and X axis direction in the second embodiment.

The shape of the beam intensity in the X axis direction shown in FIG. 8B has a moderate slope in a direction separated from the optical axis compared to the shape of the beam intensity in the Y axis direction shown in FIG. 8A. The beam intensity had a maximum value of 97.8% at the positions on the X axis direction 12.5 µm and −12.5 µm, as shown in FIG. 8B. Accordingly, a substantially uniform light irradiated the flow path 115. In this way the shape of the beam intensity in the Y axis direction and the X axis direction in the flow path 115 can be appropriately set for the collective lens 132 of the second embodiment so as to detect particles in the measurement sample flowing through the flow path 115.

Third Embodiment

Figure 7B:
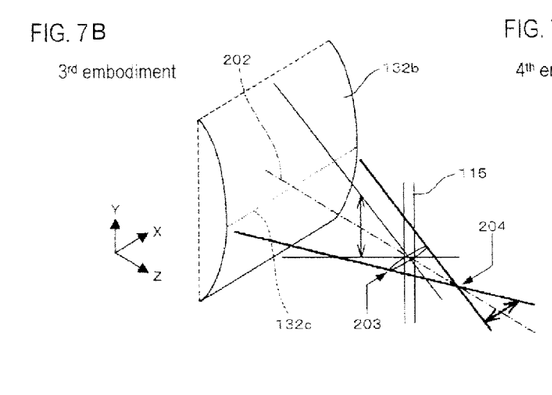
FIG. 7B is a schematic view of the collective lens exit surface and laser light convergence state in a third embodiment.

The flow cytometer of the third embodiment has a structure identical to the flow cytometer of the first embodiment with the exception that the shape of the exit surface of the collective lens 132 is different. As shown in FIG. 7B, in the third embodiment the generating line 132c of the cylindrical surface of the exit surface 132b is in the X axis direction, that is, in a direction intersecting the flow path 115 compared with the first embodiment.

The laser light 201 in this case is converged by the entrance surface 132a in the X axis direction, and focused at the position 204. Position 204 is on the Z axis positive side from the position of the flow path 115 of the flow cell 110. On the other hand, the laser light 201 is converged by the entrance surface 132a and the exit surface 132b in the Y axis direction, and focused at position 203. Position 203 matches the position of the flow path 115 of the flow cell 110. In the third embodiment, therefore, the laser light 201 irradiates the flow path 115 so that the width of the laser light 201 in a direction parallel to the flow path 115 is less than the width in a direction intersecting the flow path 115 similar to the first embodiment.

In the third embodiment, the entrance surface 132a is designed to converge the light at a position farther than the flow path 115 unlike the first embodiment. The converging of light in the Y axis direction is realized by using the convergence effect of the entrance surface 132a and the convergence effect of the exit surface 132b which has a spherical surface. In the third embodiment, therefore, the entrance surface 132a is designed to suppress aberration and distortion while considering the effect of the exit surface 132b. In the third embodiment, light irradiates the flow path 115 of the flow cell 110 in a state of low aberration and scant distortion by designing the entrance surface 132a while considering the effect of the exit surface 132b.

Fourth Embodiment

Figure 7C:
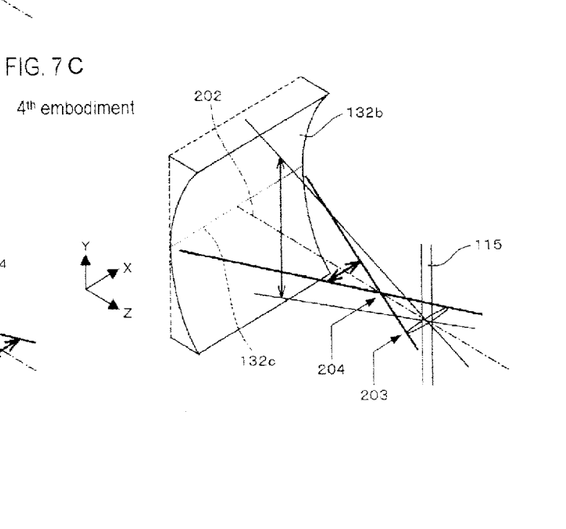
FIG. 7C is a schematic view of the collective lens exit surface and laser light convergence state in a fourth embodiment.

The flow cytometer of the fourth embodiment has a structure identical to the flow cytometer of the first embodiment with the exception that the shape of the exit surface of the collective lens 132 is different. As shown in FIG. 7C, in the fourth embodiment the exit surface 132b is a cylindrical surface of which has a concave shape and constant curvature compared to the first embodiment. The generating line 132c of the cylindrical surface of the exit surface 132b is in the X axis direction, that is, in a direction intersecting the flow path 115.

The laser light 201 in this case is converged by the entrance surface 132a in the X axis direction, and focused at the position 204. Position 204 is on the Z axis negative side from the position of the flow path 115 of the flow cell 110. On the other hand, the laser light 201 is converged by the entrance surface 132a in the Y axis direction, diffused by the exit surface 132b, and focused at position 203. Position 203 matches the position of the flow path 115 of the flow cell 110. In the fourth embodiment, therefore, the laser light 201 irradiates the flow path 115 so that the width of the laser light 201 in a direction parallel to the flow path 115 is less than the width in a direction intersecting the flow path 115 similar to the first embodiment.

In the fourth embodiment, the entrance surface 132a is designed to converge the light at a position closer than the flow path 115 unlike the first embodiment. The converging of light in the Y axis direction is realized by using the convergence effect of the entrance surface 132a and the diffusion effect of the exit surface 132b which has a spherical surface. In the fourth embodiment, therefore, the entrance surface 132a is designed to suppress aberration and distortion while considering the effect of the exit surface 132b. In the fourth embodiment, light irradiates the flow path 115 of the flow cell 110 in a state of low aberration and scant distortion by designing the entrance surface 132a while considering the effect of the exit surface 132b.

Figure 9A:
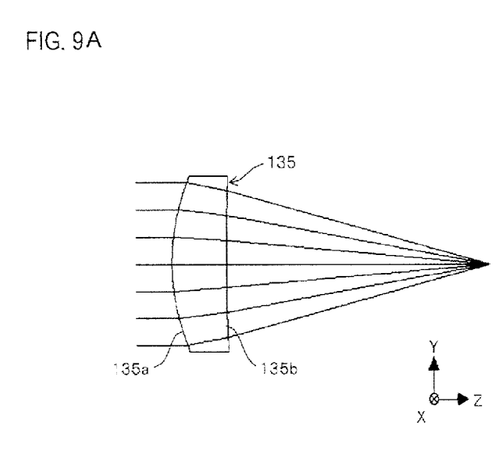
FIG. 9A is a schematic view of the collective lens and laser light convergence state in the fourth embodiment.

The spherical aberration simulation results of the fourth embodiment are described below referring to FIGS. 9A and 9B. This simulation evaluated the performance of the entrance surface 132a of the collective lens 132 of the fourth embodiment. The collective lens 132 described above converges the light in the Y axis direction through the convergence effect of the entrance surface 132a and the diffusion effect of the exit surface 132b. In the simulation, a collective lens 135 was used which had an optical axis symmetric aspheric surface as the entrance surface and an optical axis symmetric spherical surface as the exit surface instead of the collective lens 132 so as to evaluate spherical aberration by obtaining a spot diagram with the light in a circular convergence state.

The entrance surface 135a of the collective lens 135 was an optical axis symmetric aspheric surface designed according to Table 3 (1) through (4). The exit surface 135b of the collective lens 135 was an optical axis symmetric spherical surface which had the radius of curvature shown in Table 3 (5). The refractive index of the collective lens 135 was as shown in Table 3 (6). In the simulation, the size of a spot diagram was obtained when parallel rays were converged by the convergence lens 135 designed as described above, and the magnitude of the spherical aberration was evaluated. The radius and wavelength of the parallel light were as shown in Table 3 (7) and (8).

TABLE 3

Spherical aberration simulation conditions of fourth embodiment

| | | |
|---|---|---|
| 1) Entrance surface 135a radius of curvature | 7.115 mm | |
| 2) Entrance surface 135a curvature c | 0.14053 | |

TABLE 3-continued

Spherical aberration simulation conditions of fourth embodiment

| | | |
|---|---|---|
| 3) Conic constant k | −0.58578 | |
| 4) 4th-order aspheric surface coefficient α4 | 0.00002995 | |
| 5) Exit surface 135b radius of curvature | 90 mm | |
| 6) Collective lens 135 refractive index | 1.5110 | |
| 7) Parallel light wavelength | 642 nm | |
| 8) Parallel light radius | 3.24 mm | |

Figure 9B:
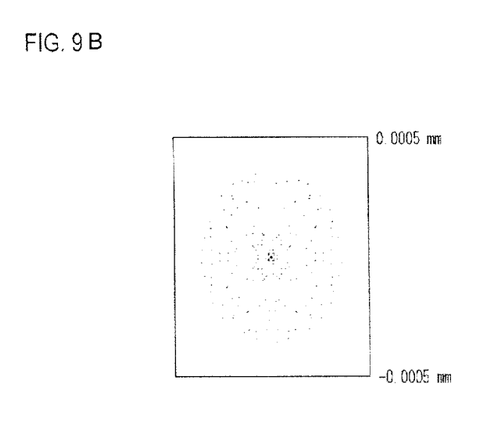
FIG. 9B shows a spot diagram in the case of the collective lens of the fourth embodiment.

As shown in FIG. 9B, the spot diagram radius was $3.548 \times 10^{-5}$ mm when parallel rays were converged by the collective lens 135.

In the simulation results, the size of the spot diagram somewhat increased compared to the simulation results of the first embodiment described referring to FIGS. 5A and 5B. However, the size of the spot diagram in the simulation results was several levels smaller in value compared to the simulation results of the collective lens 133 of the conventional example configured by a spherical lens described referring to FIGS. 4A and 4B. Thus, spherical aberration is effectively suppressed even in the collective lens 132 of the fourth embodiment compared to the collective lens of the conventional example configured by a spherical lens.

In the third embodiment, light was converged in the Y axis direction by the optical effects of both the entrance surface 132a and the exit surface 132b of the collective lens 132 similar to the fourth embodiment. Accordingly, the effect of suppressing spherical aberration identical to the fourth embodiment can be obtained by adjusting the design of the entrance surface 132a.

Fifth Embodiment

Figure 10:
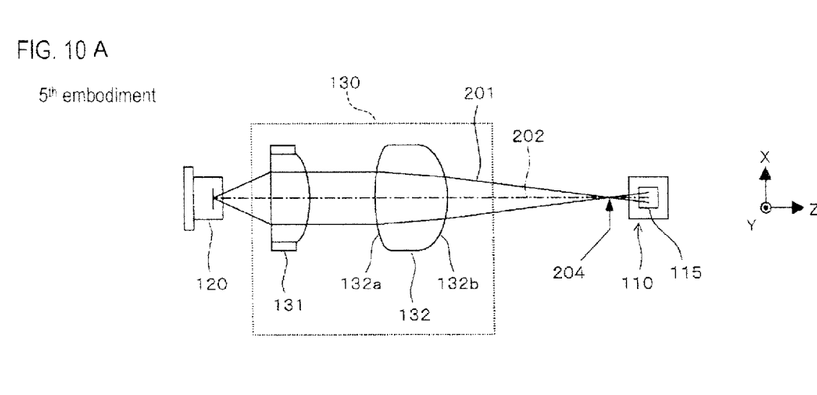
FIG. 10A is a schematic view of the structure of the flow cytometer of a fifth embodiment viewed in the Y axis negative direction and the X axis positive direction.
FIG. 10B is a schematic view of the structure of the flow cytometer of the fifth embodiment viewed in the Y axis negative direction and the X axis positive direction.

The flow cytometer of the fifth embodiment has a structure identical to the flow cytometer of the first embodiment with the exception that the shape of the exit surface of the collective lens 132 is different. As shown in FIGS. 10A and 10B, in the fifth embodiment the entrance surface 132a of the collective lens 132 is a cylindrical surface which has a convex shape and constant curvature, and the exit surface 132b is an optical axis symmetric aspheric surface compared to the first embodiment. The generating line of the cylindrical surface is parallel to the flow path 115. In the fifth embodiment, the functions of the entrance surface and the exit surface of the collective lens 132 are switched compared to the first embodiment. In FIGS. 10A and 10B, the structures other than the flow cell 110 are omitted for the sake of convenience.

The spherical aberration simulation results of the fifth embodiment are described below. In the simulation below, the size of the spot diagram was obtained when using the collective lens 132 of the fifth embodiment, and the magnitude of the spherical aberration was evaluated.

In the simulation, parallel rays impinged the entrance surface 132a, and a spot diagram was obtained at position 203 shown in FIG. 10B. The conditions of the simulation are described in Table 4 below. Note that in the simulation the entrance surface 132a is parallel to the X-Y axis in order to evaluate the magnitude of spherical aberration at position 203, that is, at the position of the flow path 115 of the flow cell 110.

TABLE 4

Spherical aberration simulation conditions of fifth embodiment

| | | |
|---|---|---|
| 1) Exit surface 132b radius of curvature | −7.6983 mm | |
| 2) Exit surface 132b curvature c | −0.12990 | |
| 3) Conic constant k | 0.11835 | |

TABLE 4-continued

Spherical aberration simulation conditions of fifth embodiment

| | |
|---|---|
| 4) 4th-order aspheric surface coefficient α4 | $6.598 \times 10^{-4}$ |
| 5) Collective lens 132 refractive index | 1.5110 |
| 6) Parallel light wavelength | 642 nm |
| 7) Parallel light radius | 3.24 mm |

In the simulation results, the radius of the spot diagram was $5.955 \times 10^{-5}$ mm when parallel rays were converged by the collective lens 132 of the fifth embodiment.

In the simulation results, the size of the spot diagram somewhat increased compared to the simulation results of the first embodiment described referring to FIGS. 5A and 5B. However, the size of the spot diagram in the simulation results was several levels smaller in value compared to the simulation results of the collective lens 133 of the conventional example configured by a spherical lens described referring to FIGS. 4A and 4B. Thus, spherical aberration is effectively suppressed even in the collective lens 132 of the fifth embodiment compared to the collective lens of the conventional example configured by a spherical lens.

Modifications

The collimating lens 131 also may be omitted in the first through fifth embodiments. In this case, the setting values of the collective lens 132 may be modified so that the laser light 201 irradiates the flow path 115 of the flow cell 110 in a shape identical to the first through fifth embodiments.

Although the curvature of the cylindrical surface in the collective lens 132 is constant in the first through fifth embodiments, the present invention is not limited to this configuration inasmuch as the curvature of the cylindrical surface need not be constant. In this case, the shape of the intensity distribution of the laser light 201 on the flow path 115 of the flow cell 110 may be a so-called top hat shape that is flatter close to the top. In this way the intensity of the light in a direction intersecting the flow path 115 can be more uniform so that a uniform light irradiates the flow path 115.

The flow cytometer 100 also may be configured so that the laser light 201 and a laser light of a different wavelength than the laser light 201 irradiate the flow path 115 of the flow cell 110 in the first through fifth embodiments. In this case, another light source is arranged in the flow cytometer 100, and emits laser light of a different wavelength than the laser light 201.

Although blood is the object of measurement in the first through fifth embodiments, urine also may be an object of measurement. The present invention is applicable to apparatuses for measuring particles in biological samples such as blood and urine.

What is claimed is:

1. A flow cytometer comprising:
 a flow cell configured to induce a flow of a sample containing object particles in a flow direction;
 a light source;
 an irradiating optical system comprises a collective lens configured to irradiate light from the light source on the flow of particles in the flow cell;
 a detector configured to detect light given off from the flow of particles that are irradiated by light;
 wherein the collective lens has an optical axis symmetric aspherical surface on a first side, and a cylindrical surface on a second side, such that the irradiated light is converged in a direction parallel to and perpendicular to the flow direction of the sample.

2. The flow cytometer of claim 1, wherein the collective lens is arranged so that a generating line of the cylindrical surface is parallel to the flow of the object particles in the flow cell.

3. The flow cytometer of claim 2, wherein the optical axis symmetric aspherical surface is configured with a shape to condense entering light at a focal point, the cylindrical surface is configured to shape the light irradiating the flow cell so that a width in the direction parallel to the flow direction is less than a width in the direction perpendicular to the flow direction.

4. The flow cytometer of claim 3, wherein the optical axis symmetric aspherical surface is on a light entrance surface of the collective lens, and the cylindrical surface is on a light exit surface of the collective lens.

5. A particle analyzer comprising the flow cytometer of claim 4 and an analyzer configured to process the output from the detector, and analyze the object particles in the sample.

6. The flow cytometer of claim 3, wherein the optical axis symmetric aspherical surface is on a light exit surface of the collective lens, and the cylindrical surface is on a light entrance surface of the collective lens.

7. A particle analyzer comprising the flow cytometer of claim 6 and an analyzer configured to process the output from the detector, and analyze the object particles in the sample.

8. The flow cytometer of claim 3, wherein the collective lens is configured with a focal length of 5 mm or greater but not more than 100 mm in the direction parallel to the flow of the particles.

9. A particle analyzer comprising the flow cytometer of claim 8 and an analyzer configured to process the output from the detector, and analyze the object particles in the sample.

10. The flow cytometer of claim 3, wherein the cylindrical surface is a convex surface.

11. A particle analyzer comprising the flow cytometer of claim 10 and an analyzer configured to process the output from the detector, and analyze the object particles in the sample.

12. The flow cytometer of claim 3, wherein the cylindrical surface is a concave surface.

13. A particle analyzer comprising the flow cytometer of claim 12 and an analyzer configured to process the output from the detector, and analyze the object particles in the sample.

14. A particle analyzer comprising the flow cytometer of claim 3 and an analyzer configured to process the output from the detector, and analyze the object particles in the sample.

15. A particle analyzer comprising the flow cytometer of claim 2 and an analyzer configured to process the output from the detector, and analyze the object particles in the sample.

16. The flow cytometer of claim 1 further comprising a collimator lens between the light source and the collective lens.

17. The flow cytometer of claim 16, wherein the irradiating optical system further comprises the collimator lens and the collective lens.

18. A particle analyzer comprising the flow cytometer of claim 16 and an analyzer configured to process the output from the detector, and analyze the object particles in the sample.

19. A particle analyzer comprising the flow cytometer of claim 1 and an analyzer configured to process the output from the detector, and analyze the object particles in the sample.

20. A flow cytometric method comprising:
flowing a sample containing object particles through a flow cell in a flow direction;
irradiating a flow of particles in the flow cell by condensing the light from a light source through a lens having an optical axis symmetric aspherical surface on a first side, and a cylindrical surface on a second side, such that the light is converged in a direction parallel to and perpendicular to the flow direction of the sample; and
detecting light given off from the flow of particles in the flow cell.

* * * * *